US008234906B2

(12) United States Patent
De Haan et al.

(10) Patent No.: US 8,234,906 B2
(45) Date of Patent: Aug. 7, 2012

(54) SENSOR FOR GASES EMITTED BY COMBUSTION

(75) Inventors: André De Haan, Mons (BE); Marc Debliquy, Petit-Enghien (BE)

(73) Assignee: Societe de Chimie Inorganique et Organique en abrege "Sochinor", Le Roeulx (BE)

( * ) Notice: Subject to any disclaimer, the term of this patent is extended or adjusted under 35 U.S.C. 154(b) by 18 days.

(21) Appl. No.: 12/311,910

(22) PCT Filed: Oct. 19, 2007

(86) PCT No.: PCT/EP2007/061247
§ 371 (c)(1),
(2), (4) Date: Nov. 30, 2010

(87) PCT Pub. No.: WO2008/046926
PCT Pub. Date: Apr. 24, 2008

(65) Prior Publication Data
US 2011/0100087 A1    May 5, 2011

(30) Foreign Application Priority Data
Oct. 19, 2006    (EP) .................................... 06122626

(51) Int. Cl.
*G01N 7/00* (2006.01)
(52) U.S. Cl. ............................ 73/23.31; 73/1.06; 438/49
(58) Field of Classification Search .................. 73/1.06, 73/23.31; 257/E21.211; 324/691; 438/49
See application file for complete search history.

(56) References Cited

U.S. PATENT DOCUMENTS

| 4,640,628 | A | * | 2/1987 | Seki et al. ...................... 374/141 |
| 4,792,433 | A | * | 12/1988 | Katsura et al. .................. 422/98 |
| 5,140,393 | A | * | 8/1992 | Hijikihigawa et al. ........ 257/252 |
| 5,147,523 | A | * | 9/1992 | Yagawara et al. ............. 204/424 |
| 5,330,855 | A | * | 7/1994 | Semancik et al. ............. 428/701 |
| 5,334,350 | A | * | 8/1994 | Friese et al. .................... 422/98 |
| 5,338,430 | A | * | 8/1994 | Parsonage et al. ............ 204/412 |
| 5,342,701 | A | * | 8/1994 | Miremadi et al. ............. 428/701 |
| 5,387,462 | A | * | 2/1995 | Debe ............................. 428/323 |
| 5,618,496 | A | * | 4/1997 | Hasumi et al. .................. 422/90 |

(Continued)

FOREIGN PATENT DOCUMENTS
EP    0 609 316    4/1997
(Continued)

OTHER PUBLICATIONS

Inoue et al. "Metal oxide semiconductor $NO_2$ sensor." Sensors and Actuators B, vol. 25, No. 1/3, Apr. 1995, pp. 388-391.

(Continued)

*Primary Examiner* — Peter MacChiarolo
*Assistant Examiner* — Samir M Shah
(74) *Attorney, Agent, or Firm* — Jacobson Holman PLLC

(57) ABSTRACT

A sensor for gases emitted by combustion, the sensor involving one or more metal oxides forming an adsorption semiconductor the electrical resistance of which changes according to the gas adsorbed, the semiconductor being a semiconductor for the direct adsorption of gases without catalyzed chemical reaction, the sensor being arranged to detect nitrogen oxides in the case of a bright fire, and/or the sensor being arranged to detect, in the case of a smoldering fire, partially unburned gases, in particular alcohols, aldehydes, ketones, carboxylic acids or amines.

6 Claims, 6 Drawing Sheets

U.S. PATENT DOCUMENTS

| | | | |
|---|---|---|---|
| 5,635,628 A | | 6/1997 | Fleischer et al. |
| 5,726,347 A | * | 3/1998 | De Haan .................. 73/31.06 |
| 5,767,388 A | * | 6/1998 | Fleischer et al. ............. 73/31.06 |
| 5,797,388 A | | 8/1998 | Nakamura et al. |
| 5,942,676 A | * | 8/1999 | Potthast et al. .............. 73/31.06 |
| 6,046,054 A | | 4/2000 | McGeehin et al. |
| 6,134,946 A | * | 10/2000 | Liu et al. ................... 73/31.06 |
| 6,165,336 A | * | 12/2000 | Maki et al. .................... 204/415 |
| 7,053,425 B2 | * | 5/2006 | Sandvik et al. ............... 257/253 |
| 7,276,745 B2 | * | 10/2007 | Nakagawa et al. ........... 257/253 |
| 7,560,409 B2 | * | 7/2009 | Pitts et al. .................... 502/228 |
| 7,791,056 B2 | * | 9/2010 | Schumann .................... 250/574 |
| 7,864,322 B2 | * | 1/2011 | Carpenter et al. ........... 356/437 |
| 2003/0217586 A1 | | 11/2003 | Gouma |
| 2004/0026268 A1 | * | 2/2004 | Maki et al. .................... 205/784 |
| 2004/0113802 A1 | * | 6/2004 | Green et al. ................. 340/632 |
| 2006/0065526 A1 | * | 3/2006 | Ono et al. .................... 204/426 |
| 2011/0100087 A1 | * | 5/2011 | De Haan et al. .............. 73/1.06 |

FOREIGN PATENT DOCUMENTS

| | | |
|---|---|---|
| EP | 0 656 111 | 2/2000 |
| EP | 0 918 985 | 10/2003 |
| GB | 2 267 967 | 12/1993 |
| JP | 03172749 A * | 7/1991 |
| JP | 04 065662 | 3/1992 |
| JP | 05 302906 | 11/1993 |
| JP | 07140101 A * | 6/1995 |

OTHER PUBLICATIONS

Tomchenko et al. "Semiconducting metal oxide sensor array for the selective detection of combustion gases." Sensors and Actuators B, vol. 93, No. 1-3, Aug. 1, 2003, pp. 126-134.

* cited by examiner

SENSOR FOR GASES EMITTED BY COMBUSTION

This is a national stage of PCT/EP07/061247 filed Oct. 19, 2007 and published in French, which has a priority of European no. 06122626.2 filed Oct. 19, 2006, hereby incorporated by reference.

SENSOR FOR GASES EMITTED BY COMBUSTION

The present invention concerns a sensor for gases emitted by combustion, said sensor comprising one or more metal oxides forming a semiconductor for the direct adsorption of gases without catalyzed chemical reaction, said semiconductor being of p type and respectively n type and having a sensitive layer arranged to detect nitrogen oxides produced by a bright fire and the electrical resistance of which decreases and respectively increases when these nitrogen oxides come into contact with this sensitive layer.

Such a sensor is known from the article entitled "Metal oxide semiconductor $NO_2$ sensor" by Tomohiro Inoue et al, which appeared in Sensors and Actuators B24-25 (1995) 388-391. The article describes an $NO_2$ sensor used for detecting exhaust gases and monitoring the quality of air by detecting the quantity of $NO_2$ in the air. The sensor comprises a semiconductor formed by metal oxides. When the semiconductor comes into contact with the $NO_2$ its resistance changes, which makes it possible to use it as an $NO_2$ detector.

In this article only the detection of $NO_2$ is described. Certainly this detector can be used for detecting exhaust gases and other gases provided that they contain $NO_2$. However, it is not only $NO_2$ that is formed during a fire. In particular, in the case of smoldering fires there is no $NO_2$ produced but rather partially unburned gases. The aforementioned article does not disclose the detection of such partially unburned gases.

In fire detection smoke detectors are also known, the ionic and optical sensors of which detect the solid particles present in the smoke. However, these types of detector have a certain number of problems since their reactivity depends in particular on the size of particles emitted. In addition, some fires, such as alcohol fires, do not emit solid particles and cannot therefore be detected. As a result these smoke detectors do not detect all types of fire.

The detection of gases by semiconductors is well known but it is important in fire detection to detect only the gases emitted during combustion in order to avoid any risk of interference and therefore false alarms.

The advantage of fire detection by means of sensors detecting the gases emitted during combustion lies essentially in the following facts. They allow much earlier detection of the fire since the speed of propagation of the gases is much greater than that of solid particles detected by ionic and optical smoke detectors. In addition, their detection spectrum may be greatly extended to all types of fire provided that they detect the gases emitted during any type of combustion. This criterion is obviously not satisfied in the case of carbon monoxide CO or $NO_2$ detectors, which normally detect only these combustion gases. This is because some types of fire emit only very little CO in bright fires or $NO_2$ in smoldering fires.

Combustion gas detectors are also particularly advantageous through the fact that they are insensitive to dust and can therefore be used in dusty environments, industrial or others.

Sensors based on metal oxides able to be used in fire detection, as for example described in U.S. Pat No. 6,046,054 or UK 2267968 A, generally use either tin oxide $SnO_2$, doped with noble metals, or double oxides $CrTiO_x$, $CrRbO_x$ or $SrTiO_3$, as for example described in EP 0609316 B1, EP 0656111 B1, U.S. Pat Nos. 5,767,388 or 5,635,628. Their essential function is to detect the emission of combustible gas and, in particular, for the detection of fire, the emission of carbon monoxide CO while attempting to avoid interfering gases. Other types of gas sensor are based on electrochemical cells that specifically detect carbon monoxide CO. Unfortunately, as they detect only the presence of a specific gas (CO), they do not detect all type of fire.

Sensors based on metal oxides, such as tin oxide $SnO_2$, gallium oxide $Ga_2O_3$, etc, work at high temperatures above 400° C. In the ambient atmosphere, their semiconductivity depends on the oxygen in the air that is adsorbed on the surface. In the presence of a combustible gas, such as carbon monoxide, hydrocarbons and partially oxidized hydrocarbons, these undergo, on the surface of the sensor, catalytic combustion with the previously adsorbed oxygen. The result is a reduction in the quantity of oxygen adsorbed on the surface and therefore a change in the electrical resistance of the sensor. These sensors are to be classed among "catalytic" sensors based on metal oxides.

These types of detector can however only be used in the context of the detection of smoldering fires for which the emission of carbon monoxide CO is sufficiently great. They do not in fact detect fires with flames that emit very little unburned residue and carbon monoxide.

Given that they detect only smoldering fires, the field of application of this type of sensor used alone is relatively small and they must generally be coupled with other types of sensor (optical, thermal, etc).

"Catalytic" sensors based on doped tin oxide $SnO_2$ or gallium oxide $Ga_2O_3$ have many interferences and withstand very poorly the standard corrosion tests in the presence of sulfur dioxide $SO_2$. In addition, their sensitivity is influenced by ambient humidity.

These sensors work at ordinary temperature on a principle of adsorption and desorption of the gases emitted during combustion. These are therefore no longer "catalytic" sensors, but sensors for "adsorption" of combustion gases on the surface of the semiconductor.

In principle, working at ordinary temperature may have a certain advantage with regard to energy consumption since the sensor does not need to be heated. The energy consumption of a sensor is in fact a very important factor since, on a monitoring line that may contain several hundreds of them, it is necessary to provide a battery supply that, in the event of a break in mains supply, must be able to maintain monitoring for 72 hours. If the consumption of each detector is too high, the quantity and cost of the batteries required become prohibitive.

However, these sensors usable at ordinary temperature have very significant fluctuations in the base signal according to the change in the composition of the atmosphere and ambient temperature. The detection of a fire can in this case be effected only by sophisticated electronic means that evaluate in particular the change in response of a sensor during predetermined periods of time.

This is because phthalocyanine is a semiconductor the semiconductivity of which depends in particular on the oxygen in the air, but in particular on natural atmospheric pollutants such as ozone and nitrogen oxides (the resistivity p fluctuating between $10^7$ and $10^9\ \Omega^{-1}$). On the other hand, in a vacuum or an inert atmosphere, it is completely insulating ($\rho \geq 10^{15}\ \Omega^{-1} cm^{-1}$).

These sensors used at ambient temperature are therefore very sensitive to the proportion of ozone $O_3$, nitrogen oxides $NO_x$ and humidity in the atmosphere. The dependency of the sensors on ozone and nitrogen oxides greatly limits their use since the sensitivity of the detectors fluctuates as the content of these atmospheric pollutants according to the season. It is therefore important to produce sensors having a much greater sensitivity to the gaseous agents to be detected, such as combustion gases, than that which they have to natural doping elements and interfering gases.

When the resistance changes in the direction of an increase, the sensitivity S of the sensors is defined as the ratio of the resistance $R_{ag}$ in the presence of the gaseous agent to be detected to the resistance $R_{amb}$ that it has to the surroundings at this instant $S_\uparrow = R_{ag}/R_{amb}$; if the resistance decreases, the sensitivity is expressed by the inverse ratio $S_\downarrow$ equals $R_{amb}/R_{ag}$.

Given that phthalocyanine is a semiconductor dependent on the ambient atmosphere, it is impossible to reduce its sensitivity to ozone by eliminating it by means of a filter since in this case the phthalocyanine becomes an insulator again. Finally, over time, the sensors produced from phthalocyanine in the form of powder as described in EP 0 918 985 B1 undergo sintering that progressively reduces their sensitivity.

The influence of humidity on the response of these sensors also constitutes a restriction on their use. This is because, as these sensors generally work on the basis of the change in their resistance as a function of time, abrupt variations in the humidity level in the air may cause false alarms (opening of bathroom doors, showers, steam in a kitchen, etc).

However, apart from the sensitivity to fluctuations in ambient atmosphere including humidity, using sensors working at ambient temperature opens up another problem related to the recovery time of the sensors after the action of an atmospheric agent of any nature: the presence of cigarette smoke, alcohol fire for fondues, candles, various domestic solvents, perfumes, miscellaneous fires, etc. The recovery time, that is to say the period of return to the usual base line by desorption of the gases adsorbed, becomes relatively long, which causes, during a strong intoxication, a memory effect lasting for a few hours to 24 hours and the detector remains non-operational during this period.

All these problems make their use very problematical in terms of fire detection since in the safety field the response must absolutely be constant, reproducible over time and at any moment.

The aim of the present invention is to produce a sensor for gases emitted by combustion that is capable of detecting both a fire with and a fire without flames, while being only a little sensitive to fluctuations in the ambient atmosphere.

For this purpose a sensor according to the invention is characterized in that the said sensitive layer is also arranged to detect partially unburned gases produced by a smoldering fire, in particular alcohols, aldehydes, ketones, carboxylic acids, or amines, and the resistance of which increases or respectively decreases when these partially unburned gases come into contact with this sensitive layer. Conductimetric sensors or resistive sensors based on semiconductor metal oxides with direct adsorption of gases without catalyzed chemical reaction thus produced do not depend on the composition of the ambient atmosphere ($O_2$, $O_3$, $NO_x$, $H_2O$, etc). This is because it was found, also surprisingly, that by detecting partially unburned gases by means of a sensor comprising semiconductor metal oxides with direct adsorption of gases without catalyzed chemical reaction, it was possible to detect a smoldering fire.

A first preferential embodiment of a sensor according to the invention is characterized in that it comprises a heating element, in particular an electric element, for heating the metal oxide to a temperature of between 150° and 350° C. This makes it possible to heat the sensor and thus to bring it into a plurality of ranges of use according to the temperature chosen. This plurality of ranges makes it possible to adjust the sensitivity of the sensor according to its end use, as for example a fire detector, tobacco smoke detector, etc.

A second preferential embodiment of a sensor according to the invention is characterized in that the metal oxide is chosen from tungsten oxide $WO_3$, chromium oxide $Cr_2O_3$, copper oxide CuO, lanthanum oxide $La_2O_3$, or certain double oxides such as $Cr_xTi_yO_3$, or a mixture of these. These metal oxides are widely available commercially.

A third preferential embodiment of the sensor according to the invention is characterized in that it is housed in a casing provided with a metal grille. The presence of the metal grille prevents fluctuations due to changes in surroundings and thus ensures better functioning of the sensor.

The invention also concerns use of one of more metal oxides forming a semiconductor with direct adsorption of gases without catalyzed chemical reaction and the electrical resistance of which changes according to the gas adsorbed in order to detect nitrogen oxides in the case of a bright fire and/or to detect, in the case of a smoldering fire, partially unburned gases, in particular alcohols, aldehydes, ketones, carboxylic acids or amines.

The invention also concerns a method of manufacturing and calibrating such a sensor.

Finally the invention concerns a method of functioning of a sensor according to the invention where the heating element is supplied with electric current either in continuous mode or in pulsed mode. These embodiments of these sensors thus make it possible to greatly limit the energy consumption.

The invention will now be described in more detail with the help of the drawings, in which.

Figure 1A:
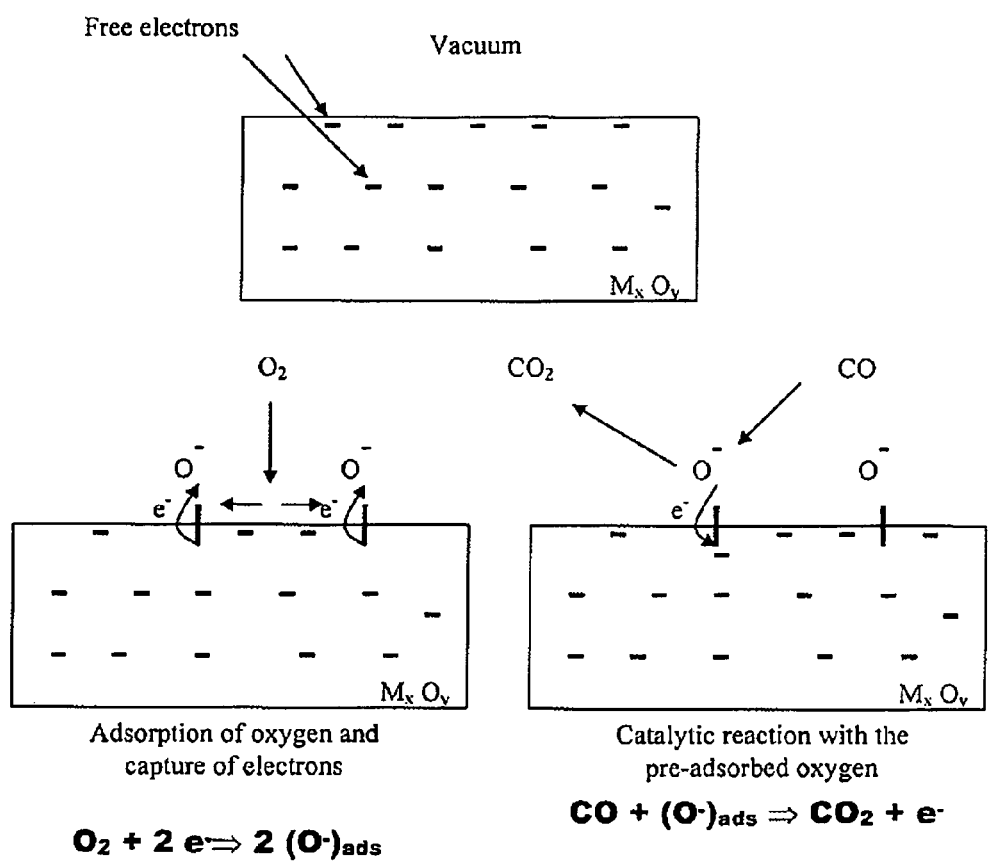
FIG. 1a illustrates the phenomenon of adsorption and catalytic reaction by means of a metal oxide for oxygen and carbon monoxide.

In the drawings the same reference has been allocated to the same component or to a similar component.

The sensors based on metal oxides, such as tin oxide $SnO_2$ or gallium oxide $Ga_2O_3$, generally work at temperatures above 400° C. In ambient atmosphere, their semiconductivity depends on the oxygen in the air that is adsorbed on the surface. FIG. 1a illustrates that, in the presence of a combustible gas, such as carbon monoxide (CO), the hydrocarbons and partially oxidized hydrocarbons undergo on the surface of the sensor a catalytic combustion with the previously adsorbed oxygen. This is because, when oxygen, present in the ambient air, comes into contact with the free electrons of the type n metal oxide present on a substrate forming part of the sensor, there will be adsorption of this oxygen and capture of free electrons.

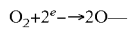

The result is a reduction in the number of free electrons and therefore in the quantity of oxygen adsorbed on the surface. On the other hand the electrical resistance of the sensor will increase. These sensors are to be classed among the so-called "catalytic" sensors based on metal oxides. In addition, when CO is present in the atmosphere, there will be a catalytic reaction with the oxygen that has been adsorbed.

$$CO + O^- \rightarrow CO_2 + e^-$$

Which will once again increase the number of free electrons and reduce the resistance of the sensor.

Figure 1B:
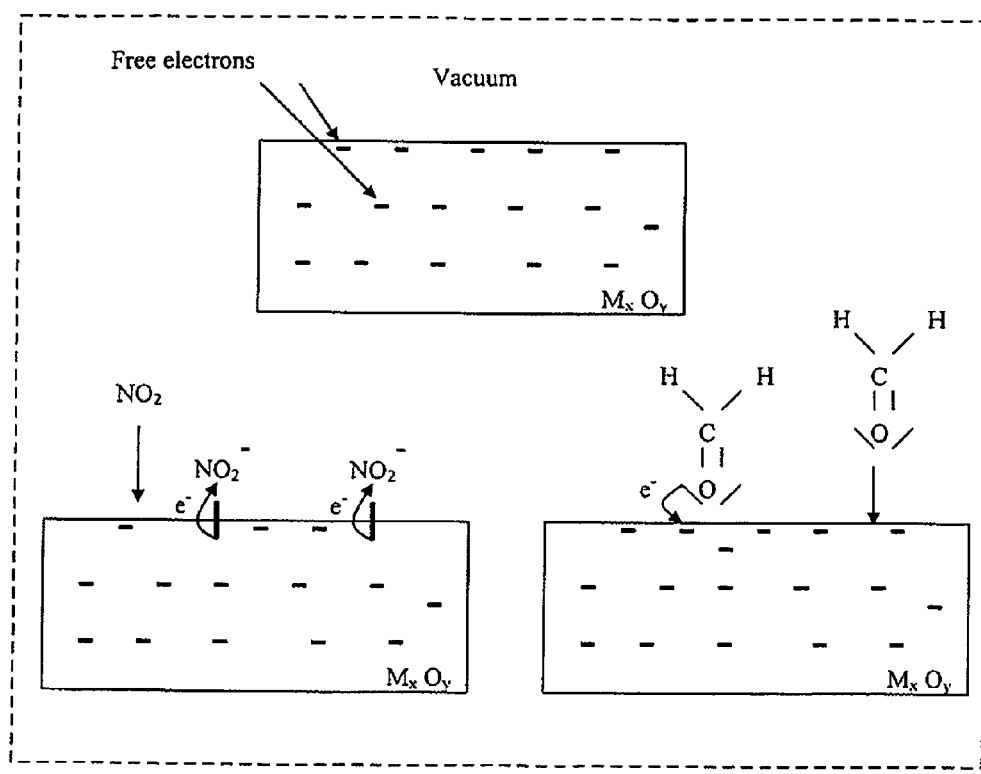
FIG. 1b illustrates the phenomenon of direct adsorption without catalytic reaction on a metal oxide for nitrogen oxide and formaldehyde.

The sensor according to the invention uses one or more metal oxides of the type with direct adsorption of the gas emitted by the combustion without catalyzed chemical reaction, as described in the previous paragraph. The particularity of these metal oxides forming a semiconductor (with direct adsorption without catalyzed chemical reaction) stems firstly from the fact that it is a case of non-conditioned semiconductors in that the semiconductivity is due amongst other things to the stoichiometric and crystalline defects in the sensitive layer itself. The natural semiconductivity is therefore not due to the presence of oxygen or atmospheric pollutants on the sensitive layer. As a result, in the case of direct-adsorption semiconductors, the detection is due to a direct and unequivocal action of the gas to be detected on the semiconductor without prior catalyzed chemical reaction with the pre-adsorbed species. FIG. 1b illustrates this phenomenon. When for example a nitrogen oxide ($NO_2$) comes into contact with the metal oxide of the sensor according to the invention, there will be a capture of free electrons $$NO_2 + e^- \rightarrow NO_2^-$$

The number of free electrons will decrease and the resistance of the sensor will increase. In the case of the presence of aldehyde ($H_2C=O$) there will be a release of free electrons and a reduction in the resistance of the sensor.

Thus, for example, during a bright fire and therefore a combustion with flames, the temperature is relatively high and, through a reaction of the oxygen and atmospheric nitrogen, nitrogen oxides form and in particular $NO_2$. It has now been found surprisingly that, once generated, this gas acts directly on the sensitive layer of the sensor without intermediate catalyzed chemical reaction (FIG. 1b). As nitrogen dioxide $NO_2$ is a powerful oxidant, it has an effect of a sensor of free electrons present in the semiconductor and in fact reduces the number of negative charge carriers in the case of a semiconductor of type n. The result is an insignificant increase in the electrical resistance of the sensor.

Conversely, in the case of a smoldering fire and therefore combustion without flames, the gases emitted by the fire are partially unburned. These gases are partially oxidized and comprise in particular alcohols, ketones, aldehydes, carboxylic acids, amines, etc. These molecules are, through their electron structure, electron donors, which will therefore by direct action increase the number of negative charge carriers of a type n semiconductor. The electrical resistance of the sensor therefore decreases to a significant extent.

The direction of these changes in resistance is obviously reversed in the presence of a type p semiconductor.

This direct action of the gases to be detected generally makes non-conditioned metal oxide sensors much more selective than conditioned catalytic sensors. The invention is therefore based on the use of one or more metal oxides forming a semiconductor with direct adsorption of gases without catalyzed chemical reaction and the electrical resistance of which changes according to the gas adsorbed in order to detect nitrogen oxides in the case of a bright fire and/or to detect partially unburned gases in the case of a smoldering fire, in particular alcohols, aldehydes, ketones, carboxylic acids or amines.

The fact that detection takes place by direct action of the gas without having recourse to catalytic combustion with oxygen also has very significant consequences on the behavior of the sensors. This is because they can in particular be used at much lower temperatures, in particular in a range situated between 150° and 350° C. This range is appreciably less than that used by usual metal oxide "catalytic" sensors and which is situated between 400° and 900° C.

Among the sensors based on non-conditioned metal oxides with direct adsorption of the gas to be detected, tungsten oxide $WO_3$, chromium oxide $Cr_2O_3$, copper oxide CuO or lanthanum oxide $La_2O_3$, can for example be cited, or even certain double oxides such as $Cr_xTi_yO_3$. These are semiconductors not conditioned by the atmosphere which, because of this, are much less sensitive to natural atmospheric fluctuations. These oxides can be used alone, in a mixture or in superimposed layers. In addition, given the lower working temperature than usual sensors based on "catalytic" oxides, the response of the sensors is solely due to equilibria of adsorption and desorption of the combustion gases that modify their electrical resistance.

Figure 2:
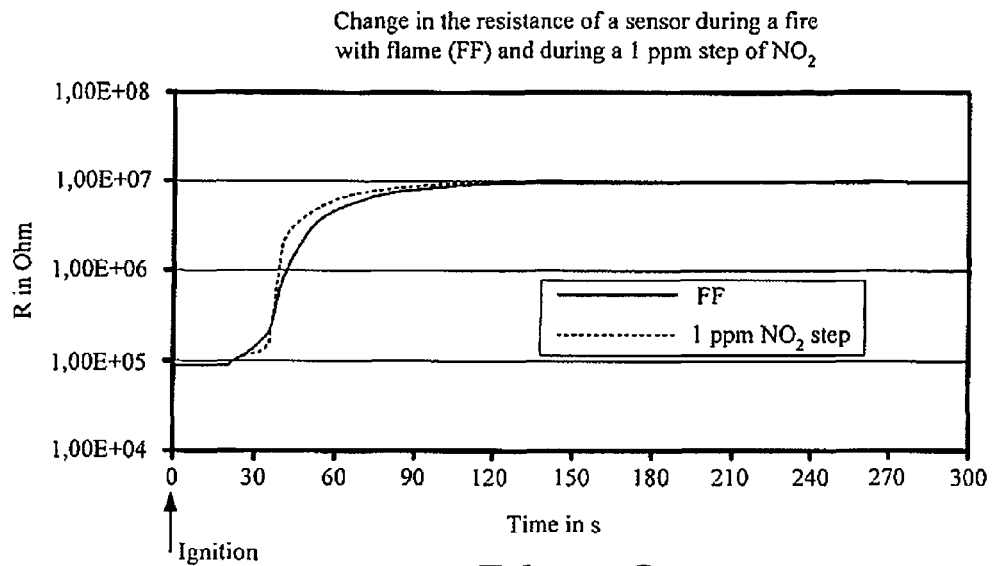
FIG. 2 illustrates the change in resistance of a sensor according to the invention during a fire with flames.
Figure 3:
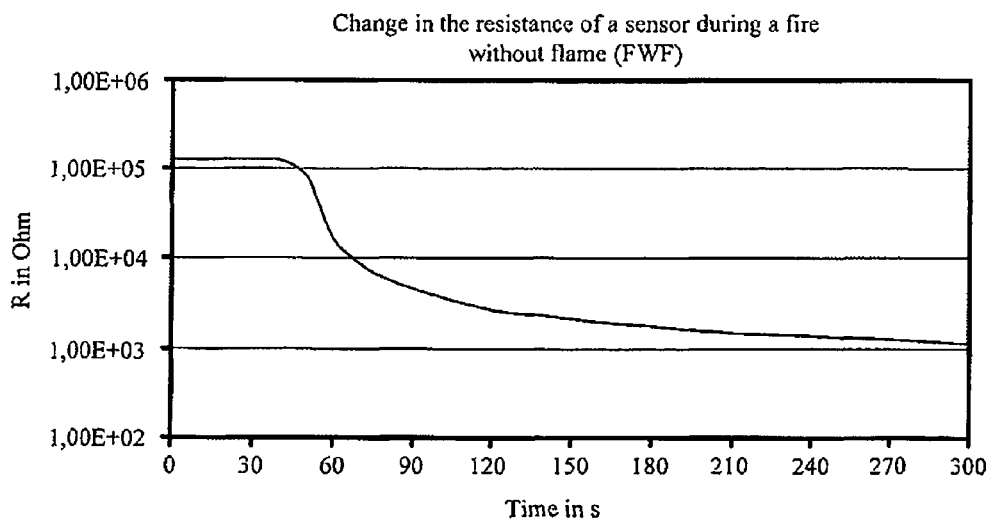
FIG. 3 illustrates the change in resistance of a sensor according to the invention during a fire without flames.

The sensors thus produced require relatively simple electronics. It suffices, according to the configuration of the sensor, to measure for example in the surroundings an electrical resistance of around $10^5$ Ω and to fix two alarm thresholds, one at $10^7$ Ω for smoldering fires and the other at $10^3$ Ω for bright fires. The fires used correspond to those described by the European (EN54-7) and American (UL 268) standards. The electrical resistance therefore changes by a factor of 100 (S≈100) in one direction or the other as illustrated in FIGS. 2 and 3. FIGS. 2 and 3 illustrate the change in the resistance of a sensor according to the invention during a fire with flame and respectively a fire without flame. With a fire with flame the resistance will increase whereas with a fire without flame it will decrease, naturally if the metal oxide used is of type n. However, overtime, the resistance will change very little in normal surroundings ($S_{max}$≈6). These changes in the surroundings are also greatly reduced when the sensor is placed in a casing, the wall of which is provided with a metal grid ($S_{max}$≈2). This is because these fluctuations in the surroundings are essentially due to a low sensitivity to ozone. As a result, when the sensor is placed in its casing, the ozone is mainly destroyed on the walls and thus has practically no more influence on the resistance of the sensor. The presence of this metal grille greatly reduces the fluctuations due to the changes in surroundings and thus ensures better functioning of the sensor.

It must also be remarked that the sensors according to the invention are largely insensitive to fluctuations in ambient humidity. These sensors can therefore not only be used under normal conditions having high fluctuations in humidity but also in more particular applications: marine environment, drying rooms, saunas, etc.

Having available sensors the temperature which is regulated also makes it possible to use them in places where the temperature conditions are between −50° and 300° C. such as for example refrigeration warehouses or steelmaking industries, cement works, etc. In these environments, the surroundings are often dusty and the ambient temperatures very diverse (low or high).

When a bright fire with flame appears (FIG. 2), the sensors detect the appearance of nitrogen dioxide $NO_2$, which is always emitted under these conditions since the flame temperature in very high and in this case the nitrogen dioxide forms by reaction of the nitrogen and the oxygen in the air. When it is a case of a type n semiconductor, the presence of nitrogen dioxide $NO_2$, which may achieve proportions of around a few ppm, reduces the number of charge carriers on the surface of the semiconductor and the electrical resistance of the sensor therefore increases to a very great extent. For example, in the case of a standardized bright heptane fire the proportion of nitrogen dioxide $NO_2$ measured by chemiluminescence reaches ~1 ppm. FIG. 2 (dotted line) shows that the response of the sensor subjected in air to a proportion of $NO_2$ of 1 ppm is exactly similar. This gas can therefore be used during a sensor calibration procedure or during sensitivity tests provided for by the standards. It should be noted that, in normal environments, the proportions of nitrogen dioxide $NO_2$ rarely exceed 50 ppb.

Figure 4:
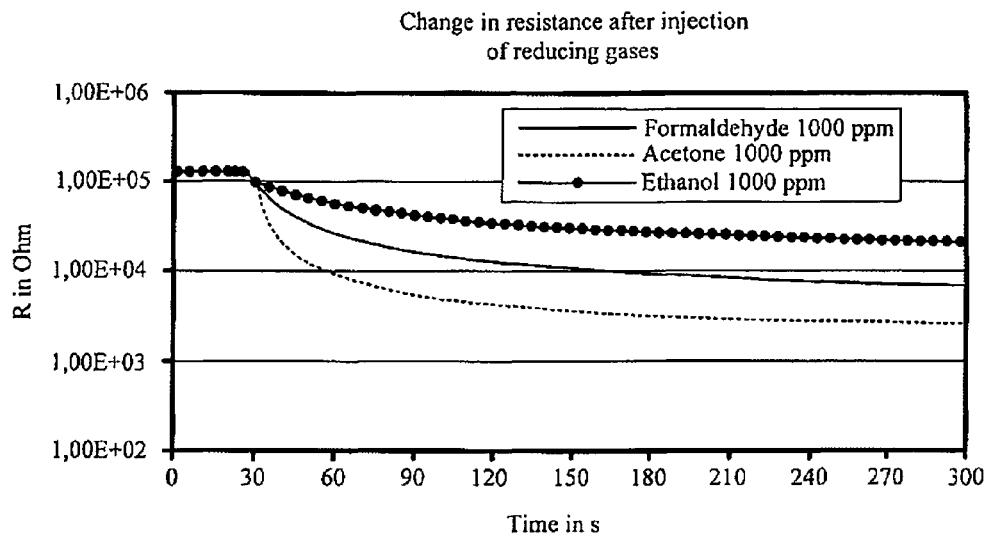
FIG. 4 illustrates the change in resistance of a sensor according to the invention in the presence of a reducing gas.

When a smoldering fire appears (FIG. 3), the temperatures reached by the fire are much lower and do not allow the formation of nitrogen dioxide. In this case, the combustions are incomplete and give rise in particular to the appearance of partially unburned gases comprising in particular alcohols ROH, aldehydes RHCO, ketones $R_1R_2CO$ or amines $R_1R_2R_3N$ oxidized to a greater of lesser extent, which are liable, while being adsorbed on the sensor, to increase on the surface the number of negative charge carriers, which has the effect of greatly reducing the resistance of a sensor produced with a type n semiconductor. FIG. 4 shows that these various types of gas having respectively the alcohol, aldehyde, ketone and even amine functions have an effect that tends towards a decrease in the electrical resistance of the sensors. FIG. 4 presents in fact the response of the sensor to injections of 1000 ppm of formaldehyde, acetone and ethanol. Smoldering fires all emit these types of gas in various proportions according to the nature of the fuel and the temperature of the fire. All these gases cause a change in the resistance of the sensor in the same direction and their effects are cumulative. Detection for smoldering fires cannot therefore not be attributed to a single gas but to all those having these types of function. The same partially unburned gases can also be used for calibrating the sensor.

It is obvious that the directions of change of the resistance according to the type of fire are reversed in the presence of a type p semiconductor.

It should also be noted that the sensors to which the present invention relates are very specific vis-à-vis gases emitted during combustion (nitrogen oxide, aldehydes, ketones, etc). This is because, unlike the "catalytic" metal oxides used at a higher temperature (>400° C.) such as for example tin oxide, they in no way react with combustible gases such as hydrogen, carbon monoxide, alkanes, methane, propane etc). This behavior is due to the fact that the change in resistance of the sensors is solely attributable to the adsorption of the combustion gases on the surface of the metal oxides and not to a catalytic reaction between this combustion gas and the oxygen previously adsorbed on the surface as is the case with "catalytic" oxides.

Figure 5:
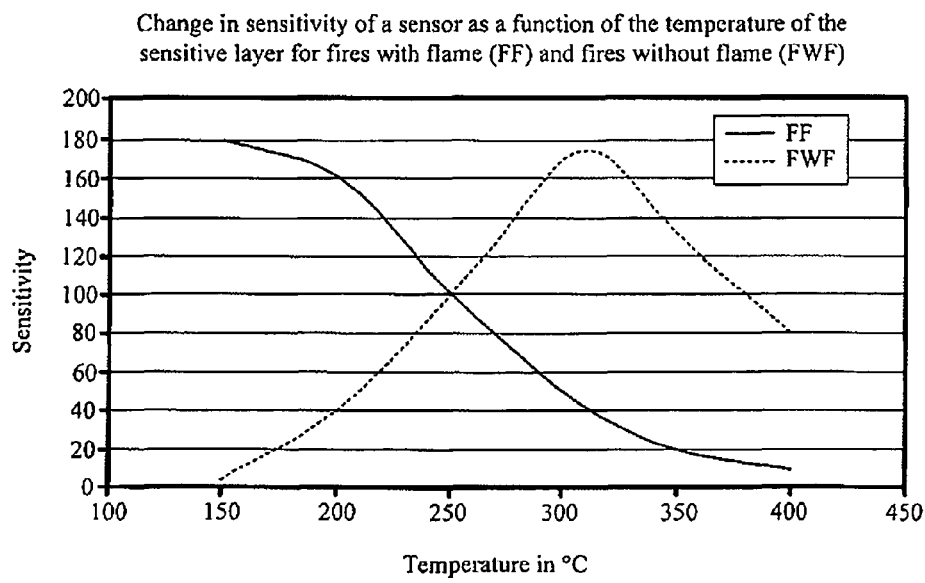
FIG. 5 illustrates the change in resistance of a sensor according to the invention as a function of the temperature of the sensor.

The choice of the nature of the semiconductor and of the operating temperature makes it possible also to increase or decrease the sensitivity of the sensor to different types of fire (with or without flames) as illustrated in FIG. 5. To allow this adjustment in temperature of the sensor, the latter is equipped with a heating element, in particular an electric element. The heating element is arranged to heat the semiconductor at a temperature situated between 150° and 350° C. Thus the sensors according to this preferential embodiment of the invention can therefore be adapted to the particular circumstances of use of the sensor according to the types of risk encountered and the place (tunnels, car parks, industries, dusty environments, overheating of electric cables, etc).

Figure 6:
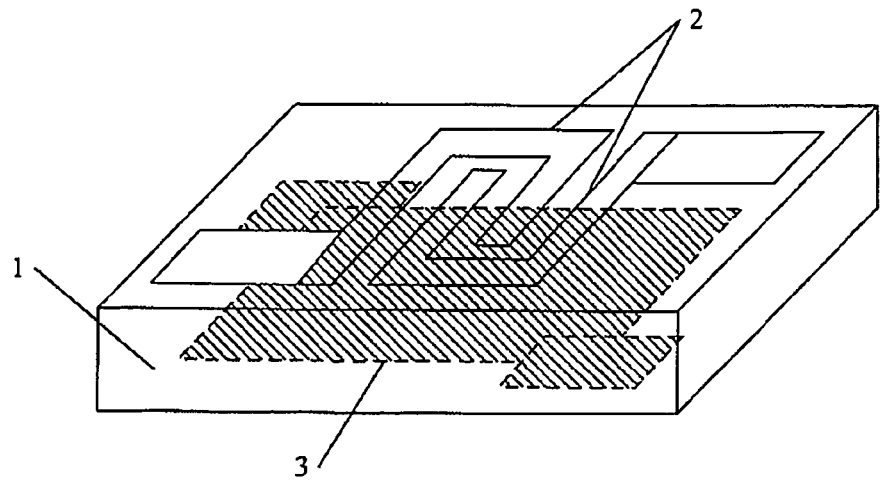
FIGS. 6, 7 and 8 illustrate embodiments of sensors according to the invention.

FIG. 6 presents a general configuration of the sensors. It comprises an insulating substrate 1 consisting for example of alumina, silicon oxidized on the surface, silicon provided with intermediate layers such as for example silicon nitride, or even other oxides or nitrides completely insulating vis-à-vis the resistances of the sensitive layers to be measured ($R_{support} >>> R_{sensitive\ layer}$). When this condition is fulfilled, the nature of the substrate has few effects on performance, it determines only the methods of implementation and therefore the consumption of electrical energy.

This substrate is conventionally provided with two interdigitated electrodes 2 consisting of a noble metal such as for example gold, platinum, etc, or even ruthenium oxide $RuO_2$. The design of the circuit depends on the type of substrate used. For example, on alumina supports it can be produced by the screen printing of inks containing the metals to be deposited or by the deposition of the metal powder (dispersed in a solvent and spread in a thin layer) followed by laser sintering. On silicon-based substrates, the electrodes can be produced by the usual photolithography techniques in the field of microelectronics.

The substrate is preferably also provided with the heating element formed by a heating element 3 consisting either of polycrystalline silicon (also referred to as polysilicon) or ruthenium oxide or a coil of noble metal such as for example platinum the electrical resistance of which has an excellent temperature coefficient (0.3%/° K), which will make it possible to precisely fix the working temperature of the sensor. The deposition of this element can be achieved by the same techniques as those used for the deposition of the electrodes. This heating element can be situated according to the configuration on one or other face of the substrate. This heating element preferably comprises temperature adjustment means arranged so as, according to the temperature of use, to adjust the sensitivity of the sensor either to detect all types of fire or to detect the said smoldering fires, or to detect the said bright fires. These adjustment means can be formed by using a variable resistance as an electric element or by varying the electric current supplying the electric element.

The surface comprising the electrodes is covered by the sensitive layer consisting of the adsorption semiconductor metal oxides not conditioned by the ambient atmosphere. The depositions can be effected by different techniques according to their field of application.

The nature of the metal oxides, the techniques used for the deposition of the sensitive layer and the conditions of use such as the temperature of the sensor can also be differentiated according to the field of application.

This is because, as described in the example embodiments, the fire detection is not solely reduced to the risks of fire in the domestic field or in the tertiary field (building, administration, hospitals, hotels, etc). It is also important to have available sensors able to be used for example in dusty industrial environments, in covered car parks, in tunnels, refrigerated warehouses, etc.

The deposits of sensitive layer can be produced on the supports by screen printing with special inks. These are obtained by the dispersion of the direct-adsorption semiconductor metal oxide powder in an organic solvent that contains the appropriate additives (surfactants, thickening agents, etc). The effect of these additives is in particular to keep the solid particles in suspension and to prevent coagulation thereof. It is therefore important to fix their surface charge and their surface electrical potential ζ so that they repel each other and do not agglomerate. The size of the oxide particles dispersed in these inks is in between 0.005 and a few μ.

In a first embodiment of the invention, the substrate consists of a 3×3 mm $Al_2O_3$ wafer 0.5 mm thick, the electrodes disposed in interdigitated double combs have for example a width of 150 μm and a spacing of 200 μm. The heating element ($R_{heat}$) situated on the same face is made from platinum and has a resistance at 25° C. of for example 17 Ω. According to the field of use, the temperature will be fixed between 150° and 350° C., which will correspond in the example chosen to resistances fixed by electronic regulation at respectively 25.6 and 33.8 Ω.

The sensitive layer is deposited either by a sol-gel method when the size of the particles is very small (<10 μm) or by screen printing of a suitable ink containing in particular the direct-adsorption semiconductor metal oxides of the gas or gases to be detected. The layer is then subjected to drying and thermal elimination of the adjuvants in the ink. The process of deposition by sol-gel or screen printing can be repeated a certain number of times (one or more layers identical or different) according to the sensitivity that it is wished to confer on it.

When the temperature is fixed at a mean value of 250° C. ($R_{heat}$=11.7 Ω), the results obtained in this configuration are those described by FIGS. 2 and 3, which corresponds to sensitivities S of approximately 100 for smoldering fires and fires with flames.

When the temperature is fixed at a lower value, around 200° C. the sensitivity S is situated around 50 for smoldering fires and 200 for fires with flames.

Conversely, when the temperature is fixed at a higher value, around 300° C., the sensitivity S is situated around 250 for smoldering fires and 30 for fires with flames.

FIG. 5 illustrates the change in the sensitivity S according to the temperature T for these two types of fire. According to the type of risk to be covered and the place of use, the temperature can therefore be adjusted to the most suitable value.

In this first configuration, according to the temperature to be achieved, the electrical energy consumption is situated around 300 mW.

In conventional fire detection, where no interference is wished for and it is wished to respond perfectly to all types of standard fire as described by FIGS. 2 and 3, it is possible to deposit up to six layers of "adsorption" oxides, which determines the thickness of the layers, which thus changes for example between 5 and 50 μ. The thickness is in fact a determining factor in the sensitivity of the sensor.

For example, if it is wished to produce not a fire detector but rather a tobacco smoke detector, the sensitivity is increased by reducing the number of layers for example to 1 and maintaining the temperature in the range that increases the sensitivity to smoldering fires (high temperature). Under these conditions, the presence of a smoker is easily detected since the sensitivity S reaches the value 30 in a few minutes for a cigarette half consumed in a room measuring 6×4×4 m.

Likewise, for sensors with a small number of layers, the overheating (without apparent combustion or emission of visible smoke) of electric cables can easily be detected. This is because, although combustion proper has not yet commenced, the gases occluded in the sheath of the cable are degassed. Thus, for example, in an electric cubicle measuring 0.5×1.2×2 m, the simple overheating of an electric cable 10 cm long and 1.5 $mm^2$ at 80° C. already causes a change in the resistance of the sensor by a factor of 100 (S=100) in approximately 2 minutes. The results are obviously identical if it is a case of the overheating of a printed circuit rather than a cable or more generally the overheating of any electrical component comprising organic polymers in its structure.

In a second configuration (FIG. 5), the sensor is produced on oxidized or nitrided silicon supports (4=substrate, 1=oxide or nitride). These 2×2×1.5 mm supports are hollowed out in the mass of the silicon substrate on their bottom face so as to greatly reduce their thickness at the point where the electrodes and the heating element (3) will be disposed. These electrodes (2) are deposited by photolithography techniques conventional in microelectronics. In this case, either the top surface of the sensor is made rough so that the oxide layers can be deposited as before by screen printing, by a sol-gel method or by cathodic sputtering, or the surface is smooth and only the last two techniques can be used.

Cathodic sputtering uses, for example, when producing a layer of tungsten oxide $WO_3$, a tungsten cathode and a low partial pressure of oxygen.

For heating, another configuration consists of encircling the electrodes, on the top face, with a platinum or polysilicon coil.

The sensors thus produced have the same performance as those produced on alumina $Al_2O_3$ but the electrical consumption is reduced by a factor of fifteen (that is to say for example 20 mW).

Another way of further reducing the energy consumption consists of operating the sensor in pulsed rather than continuous mode. It is a question, in this case, of supplying the heating element of the sensor for example for 2 seconds every 10 or 20 seconds. The duration of heating and consequently the electrical consumption is greatly reduced and it is thus possible, according to the heating and pause durations chosen, to once again reduce the electrical consumption by a factor of five to ten.

Figure 7:
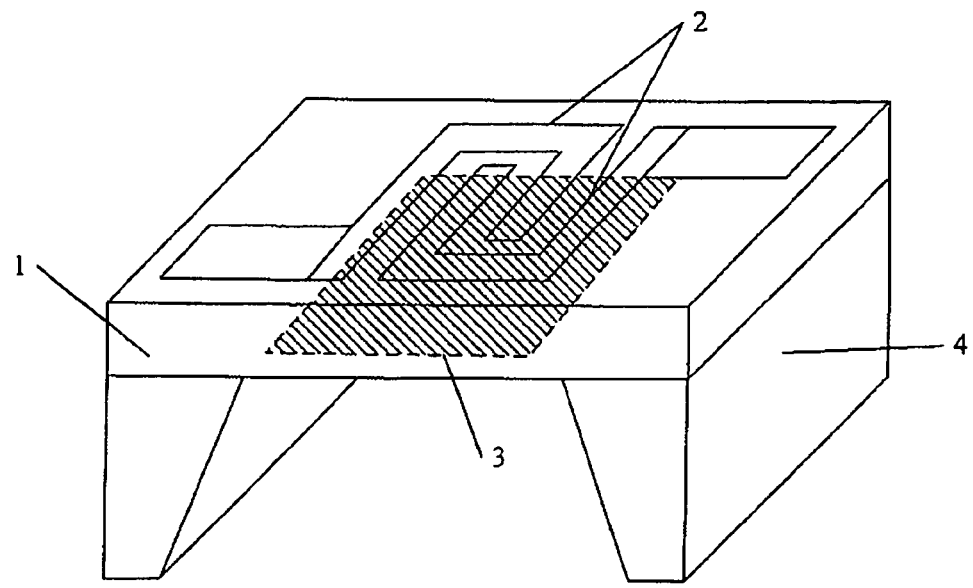
Figure 8:
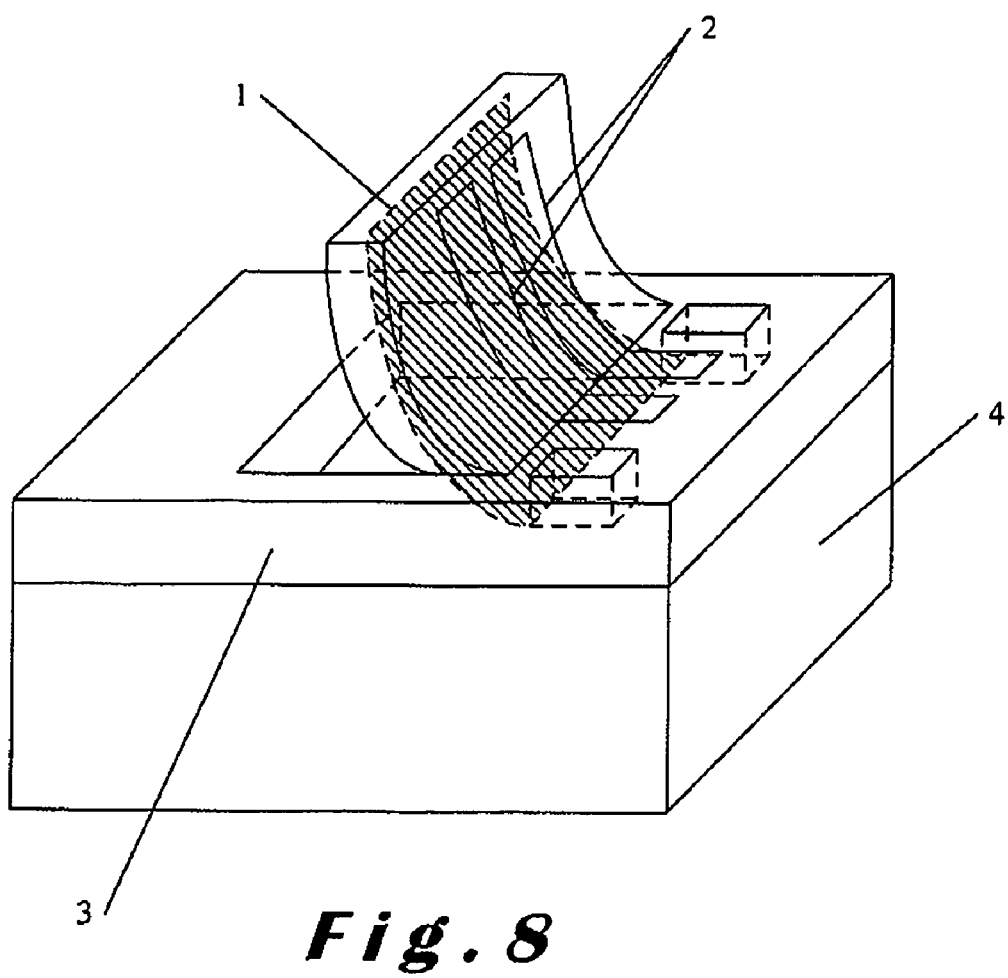

In a third configuration shown in FIG. 6 (not to scale), the silicon substrate (4) has a rectangular shape, the dimensions of which are for example 2×2 mm. On this substrate, various layers either of silicon dioxide or nitride are formed or deposited on the top face 3. This substrate is also hollowed out on its bottom face until its thickness is reduced for example to 5 μm. Above the hollowed-out surface and in a rectangle of for example 50×100 μm, the electrodes 2, the heating element 1 and the sensitive layer are deposited as in the previous example. Finally, a strip corresponding to the rectangle where the sensitive layer is situated is cut on three sides (FIG. 7). The fourth side making it possible to establish the electrical contacts to the electrodes and to the heating element. Under the effect of the mechanical expansion and compression tensions of the layers of silicon or silicon dioxide and/or nitride and under the effect of temperature this strip lifts.

As a result, when the element is supplied in continuous or pulsed mode, only this extremely thin strip is heated and the energy consumption is once again greatly reduced (by a factor of two to ten). The behavior of these sensors vis-à-vis the various types of fire is obviously the same, since the sensitivity does not depend on the extent of the surface of the sensor.

All these actions make it possible, according to the risk to be covered and the field of application, to adapt the detector to the requirements actually encountered.

What is claimed is:

1. A method of manufacturing a sensor for gases emitted by combustion, said sensor comprising one or more metal oxides forming a semiconductor directly adsorbing gases without a catalyzed chemical reaction, said semiconductor being of p type or respectively n type and having a sensitive layer having an electrical resistance, wherein (i) the sensitive layer detects nitrogen oxides produced by a bright fire and the electrical resistance of which decreases or respectively increases upon contact with the nitrogen oxides and (ii) the sensitive layer detects one or more partially unburned gases selected from a group consisting of alcohols, aldehydes, ketones, carboxylic acids and amines produced by a smoldering fire and the electrical resistance of which increases or respectively decreases upon contact with the one or more partially unburned gases, wherein the metal oxide is deposited once or several times by one of ink screen printing, sol-gel and sputtering techniques on an alumina or silicon insulating substrate covered with layers of silicon oxides or nitrides, said substrate then being provided with electrodes and a heating element for maintaining the temperature of the layer of oxides at a temperature chosen between 150° C. and 350° C.

2. A method of calibrating a sensor, said sensor comprising one or more metal oxides forming a semiconductor directly adsorbing gases without a catalyzed chemical reaction, said semiconductor being of p type or respectively n type and having a sensitive layer having an electrical resistance, wherein (i) the sensitive layer detects nitrogen oxides produced by a bright fire and the electrical resistance of which decreases or respectively increases upon contact with the nitrogen oxides and (ii) the sensitive layer detects one or more partially unburned gases selected from a group consisting of alcohols, aldehydes, ketones, carboxylic acids and amines produced by a smoldering fire and the electrical resistance of which increases or respectively decreases upon contact with the one or more partially unburned gases, wherein the sensitivity of the sensor is calibrated by the nitrogen oxides in the case of bright fires and by the alcohols, aldehydes, ketones, carboxylic acids and amines in the case of smoldering fires.

3. A method for detecting a fire with or without a flame, wherein said fire produces at least one gas selected from a group consisting of a nitrogen oxide and one or more partially unburned aldehydes, ketones, carboxylic acids and amines, said method comprising:
 providing a p type or respectively n type semiconductor sensor having a sensitive layer comprising one or more metal oxides;
 setting a reference value for an electrical resistance of said sensitive layer when not in contact with said at least one gas;
 directly adsorbing upon contact the at least one gas by the semiconductor without a catalyzed chemical reaction;
 differentially detecting when a decrease or an increase in the electrical resistance occurs with respect to said reference value;
 upon detecting a resistance decrease (i) identifying the nitrogen oxide for the p type semiconductor and (ii) identifying one or more of the aldehydes, ketones, carboxylic acids and amines for the n type semiconductor;
 upon detecting a resistance increase (i) identifying one of the aldehydes, ketones, carboxylic acids and amines for the p type semiconductor and (ii) identifying the nitrogen oxide for the n type semiconductor;
 signaling presence of said fire upon identifying said at least one gas.

4. The method as claimed in claim 3, wherein said reference value is set to $10^7$ Ω for a fire without a flame and to $10^3$ Ω for a fire with a flame for an n type semiconductor.

5. The method as claimed in claim 3, wherein a metal grid is provided in front of said sensor.

6. The method as claimed in claim 3, wherein said sensor is heated to a temperature between 150° C. and 350° C.

* * * * *